United States Patent [19]

Guillemin et al.

[11] 4,316,891

[45] Feb. 23, 1982

[54] EXTENDED N-TERMINAL SOMATOSTATIN

[75] Inventors: Roger C. L. Guillemin, La Jolla; Nicholas C. Ling, San Diego; Fred S. Esch, San Diego; Peter Bohlen, Encinitas; Paul E. Brazeau, Jr., San Diego, all of Calif.

[73] Assignee: The Salk Institute for Biological Studies, San Diego, Calif.

[21] Appl. No.: 159,801

[22] Filed: Jun. 14, 1980

[51] Int. Cl.³ ............... A61K 37/00; C07C 103/52
[52] U.S. Cl. ....................... 424/177; 260/112.5 S
[58] Field of Search ................ 260/112.5 S; 424/177

[56]  References Cited

U.S. PATENT DOCUMENTS

| | | | |
|---|---|---|---|
| 3,904,594 | 9/1975 | Guillamin et al. | 260/112.5 S |
| 3,931,140 | 1/1976 | Sarantakis | 260/112.5 S |
| 3,998,795 | 12/1976 | Sarantakis | 260/112.5 S |
| 4,055,553 | 10/1977 | Chai et al. | 260/112.5 S |
| 4,093,609 | 6/1978 | Sarantakis | 260/112.5 S |

OTHER PUBLICATIONS

J. Endocr. (1978) 77, 429–430.

Biochem. and Biophys. Res. Communications 85, (1978) 701–708.

*Primary Examiner*—Delbert R. Phillips
*Attorney, Agent, or Firm*—Fitch, Even, Tabin, Flannery & Welsh

[57] ABSTRACT 28-member residue and 25-member residue peptides have been synthesized containing the tetradecapeptide somatostatin that are more potent than somatostatin. Somatostatin-28 has the formula:

H-Ser-Ala-Asn-Ser-Asn-Pro-Ala-Met-Ala-Pro-Arg-Glu-Arg-Lys-

Ala-Gly-Cys-Lys-Asn-Phe-Phe-Trp-Lys-Thr-Phe-Thr-Ser-Cys-OH.

The three N-terminal amino acid residues are absent in somatostatin-25. Somatostatin-28 or somatostatin-25 or a pharmaceutically acceptable addition salt thereof, dispersed in a pharmaceutically acceptable liquid or solid carrier, can be administered to mammals in the same manner as somatostatin.

6 Claims, No Drawings

EXTENDED N-TERMINAL SOMATOSTATIN

The invention described herein was made in the course of work under a grant or award from the Department of Health and Human Services.

This invention is directed to peptides relating to the tetradecapeptide somatostatin and to methods for pharmaceutical treatment of mammals using such peptides. More specifically, the invention relates to peptides of between 28 and 25 amino acid residues which contain the tetradecapeptide somatostatin, to pharmaceutical compositions containing such peptides, to the synthesis of such peptides and to methods of treatment of mammals using such peptides.

BACKGROUND OF THE INVENTION

The tetradecapeptide somatostatin was characterized by Guillemin et al. and is described in U.S. Pat. No. 3,904,594 (Sept. 9, 1975.) The tetradecapeptide has the formula:

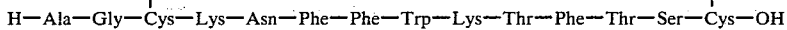
H—Ala—Gly—Cys—Lys—Asn—Phe—Phe—Trp—Lys—Thr—Phe—Thr—Ser—Cys—OH wherein there is a bridging bond between the sulfhydryl groups of the two cysteinyl amino acid residues. The tetradecapeptide in its linear form (sometimes referred to as dihydrosomatostatin), wherein this bridging bond is not present and is replaced by hydrogen, is for purposes of this application considered to be included in the definition "somatostatin" as it appears to have substantially the same biological activity.

Somatostatin and many analogs of somatostatin exhibit activity in respect to the inhibition of growth hormone (GH) secretion from cultured, dispersed rat anterior pituitary cells in vitro and also in vivo and with respect to the inhibition of insulin and glucagon secretion in vivo in the rat and in other mammals. Somatostatin has also been found to inhibit the secretion of gastrin and secretin by acting directly upon the secretory elements of the stomach and pancreas respectively. In addition to being found in the hypothalamus, somatostatin also occurs in neuronal elements and axonal fibers in multiple locations in the central nervous system, including the spinal cord, and in discrete secretory cells of classical epithelial layers in all the parts of the stomach, gut, and pancreas, in which it was first recognized as having an inhibitory effect. The powerful inhibitory effects of somatostatin on the secretion not only of GH but also of insulin and glucagon have led to studies of a possible role of somatostatin in the management or treatment of juvenile diabetes and have proved useful in studying the physiological and pathological effects of these hormones on human metabolism. Such studies, showing that somatostatin lowers plasma glucose concentrations in normal man despite its inhibitory effect on insulin, have provided the first clear-cut evidence that glucagon has an important physiological role in human carbohydrate homeostasis.

In juvenile-type diabetics, somatostatin diminishes fasting hyperglycemia by as much as 50 percent in the complete absence of circulating insulin. Somatostatin impairs carbohydrate tolerance in normal humans given oral or intravenous glucose by inhibiting insulin secretion; however, carbohydrate tolerance after ingestion of balanced meals is improved in patients with insulin-dependent diabetes mellitus through the supression of excessive glucagon responses. The combination of somatostatin and a suboptimal amount of exogenous insulin (which by itself prevents neither excessive hyperglycemia nor hyperglucagonemia in response to meals) completely prevents plasma glucose concentrations from rising after meal ingestion in insulin-dependent diabetics. Through its suppression of glucagon and GH secretion, somatostatin has also been shown to moderate or prevent completely the development of diabetic ketoacidosis after the acute withdrawal of insulin from patients with insulin-dependent diabetes mellitus.

In view of its ability to inhibit the secretion of such hormones, somatostatin may be therapeutically employed in clinical conditions for the treatment of acromegaly, pancreatic islet cell tumors and diabetes mellitus. Because somatostatin has a relatively short duration of action, apparently because it is inactivated by peptidases when administered in vivo, the search has continued for longer-acting somatostatin materials, as well as for somatostatin analogs which are more potent than somatostatin or which are both more potent and exhibit dissociated inhibitory functions.

SUMMARY OF THE INVENTION

It has been found that 28- and 25-residue peptides (which contain the 14 residue peptide somatostatin) that have been prepared and purified so as to be in substantially pure form (i.e. substantially free of the remainder of a crude biological extract or of related synthetic replicates), when tested in vitro, are more potent than somatostatin in inhibiting the release of GH and when administered to mammals in effective amounts, will more effectively inhibit the release of GH. The 28-member peptide is hereinafter referred to as somatostatin-28 and has the formula:

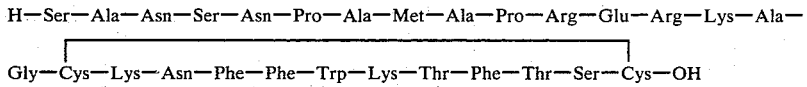
H—Ser—Ala—Asn—Ser—Asn—Pro—Ala—Met—Ala—Pro—Arg—Glu—Arg—Lys—Ala—
Gly—Cys—Lys—Asn—Phe—Phe—Trp—Lys—Thr—Phe—Thr—Ser—Cys—OH The 25-member peptide is hereinafter referred to as somatostatin-25 and has the formula:

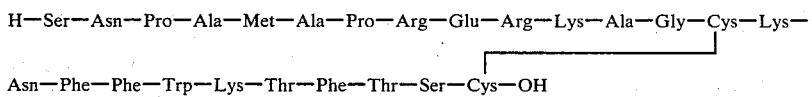
H—Ser—Asn—Pro—Ala—Met—Ala—Pro—Arg—Glu—Arg—Lys—Ala—Gly—Cys—Lys—
Asn—Phe—Phe—Trp—Lys—Thr—Phe—Thr—Ser—Cys—OH Pharmaceutical compositions in accordance with the invention include somatostatin-28 or somatostatin-25 or a nontoxic addition salt thereof, dispersed in a pharmaceutically acceptable liquid or solid carrier. The administration of somatostatin-28 or somatostatin-25 or a pharmaceutically acceptable addition salt thereof to mammals in accordance with the invention may be carried out for the regulation of secretion of growth hormone or of the secretion of insulin and/or glucagon. Novel syntheses of somatostatin-28 and of somatostatin-25 and novel intermediates produced as a part of such syntheses are also described.

DETAILED DESCRIPTION OF THE PREFERRED EMBODIMENTS

Somatostatin-28 has been earlier isolated from porcine intestinal extract and has recently been isolated from ovine hypothalmic extracts wherein the shorter somatostatin-25 peptide was also found. Synthesis of both somatostatin-28 and somatostatin-25 have now been carried out, the synthetic peptides have been carefully purified and the synthetic peptides of at least about 95% purity have been subjected to extended biological testing and have proved to be more potent than somatostatin.

The nomenclature used to define the peptides is that specified by Schroder and Lubke, "The Peptides," Academic Press (1965), wherein in accordance with conventional representation the amino group appears to the left and the carboxyl group to the right. Where the amino acid residue has isomeric forms, it is the L-form of the amino acid that is represented unless otherwise expressly indicated.

By somatostatin-28 is meant the 28-member peptide of the following formula:

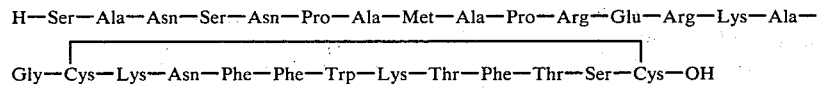

as well as the linear form thereof wherein the bridge between the sulfhydryl groups of Cys residues is not present and is replaced by hydrogen.

By somatostatin-25 is meant the 25-amino acid residue peptide having the following formula:

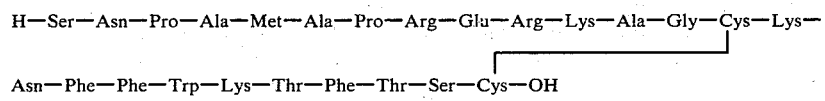

as well as the linear form thereof wherein the bridge between the sulfhydryl groups of the Cys residues is likewise replaced by hydrogen.

It can be seen that the difference between somatostatin-28 and somatostatin-25 is the inclusion of the three amino acid moieties Ser-Ala-Asn on the amino terminal of the smaller peptide. 26- and 27-residue peptides including one or two of the residues missing in somatostatin-25, at the amino terminal end thereof, are also included in the invention and are of interest from the same biological standpoint.

The peptides are synthesized by a suitable method, such as by exclusively solid-phase techniques, by partial solid-phase techniques, by fragment condensation, by classical solution addition, or by the employment of recently development recombinant DNA techniques. For example, the techniques of exclusively solid-state synthesis are set forth in the textbook "Solid-Phase Peptide Synthesis," Stewart and Young, Freeman and Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues linked to the side-action protecting groups.

Also considered to be within the scope of the present invention are intermediates of the formula:

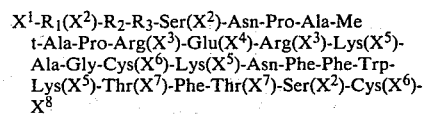

wherein: $R_1$ is Ser or des $R_1$; $R_2$ is Ala or des $R_2$; $R_3$ is Asn or des $R_3$; $X^1$ is either hydrogen or an α-amino protecting group. The α-amino protecting groups contemplated by $X^1$ are those known to be useful in the art in the step-wise synthesis of polypeptides. Among the classes of α-amino protecting groups covered by $X^1$ are (1) acyl-type protecting groups, such as formyl, trifluoroacetyl, phthalyl, toluenesulfonyl(tosyl), benzensulfonyl, nitrophenylsulfenyl, tritylsulfenyl, o-nitrophenoxyacetyl, chloroacetyl, acetyl, and α-chlorobutyryl; (2) aromatic urethan-type protecting groups, such as benzyloxycarbonyl (CBZ) and substituted CBZ, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl (trityl), benzyl; (7) trialkylsilane groups, such as trimethylsilane. The preferred α-amino protecting group is BOC.

$X^2$ and $X^7$ are protecting groups for the hydroxyl group of Thr and Ser and are selected from the group consisting of acetyl, benzoyl, tert-butyl, trityl, tetrahydropyranyl, Bzl, 2,6-dichlorobenzyl and CBZ. the preferred protecting group is Bzl. $X^2$ and/or $X^7$ can be hydrogen, which means there is no protecting group on the hydroxyl group.

$X^3$ is a protecting group for the guanidino group of Arg selected from the group consisting of nitro, tosyl, benzyloxycarbonyl, adamantyloxycarbonyl, and BOC, or is hydrogen;

$X^4$ is hydrogen or an ester-forming protecting group for the γ-carboxyl group of Glu and is selected from the group consisting of Bzl, 2,6-dichlorobenzyl, CBZ, methyl and ethyl.

$X^5$ is hydrogen or a protecting group for the side chain amino substituent of Lys. Illustrative of suitable side chain amino protecting groups are benzyl (Bzl), 2-chlorobenzyloxycarbonyl (2-Cl-CBZ), benzyloxycarbonyl (Z), tosyl(TOS), t-amyloxycarbonyl and BOC. The selection of a side chain amino protecting group is not critical except that it must be one which is not removed during deprotection of the α-amino groups during the synthesis. Hence, the α-amino protecting group and the side chain amino protecting group cannot be the same.

$X^6$ is a protecting group for Cys selected from the group consisting of p-methoxybenzyl, p-methylbenzyl, acetamidomethyl, trityl and benzyl(Bzl). The preferred protecting group is p-methoxybenzyl. $X^6$ can be hydrogen which means that there is no protecting group on the sulfur group.

$X^8$ is selected from the class consisting of OH, OCH$_3$, esters, amides, hydrazides and benzyl ester or hydroxymethyl ester anchoring bond used in solid phase synthesis linked to a solid resin support represented by the formulae:

—O—CH$_2$-polystyrene resin support and

O—CH$_2$-benzyl-polystyrene resin support

The polymer is preferably a copolymer of styrene with about 0.5 to 2% divinyl benzene as a cross linking agent which causes the polystyrene polymer to be completely insoluble in certain organic solvents. In the formula, at least one of $X^1$, $X^2$, $X^3$, $X^4$, $X^5$, $X^6$, $X^7$, and $X^8$ is a protecting group.

In selecting a particular side chain protecting group to be used in the synthesis of the peptides, the following rules are followed: (a) the protecting group must be stable to the reagent and under the reaction conditions selected for removing the α-amino protecting group at each step of the synthesis, (b) the protecting group must retain its protecting properties and not be split off under coupling conditions, and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal end of the peptide by coupling a protected α-amino acid to a suitable resin.

Such a starting material can be prepared by attaching α-amino- and S-protected Cys to a chloromethylated resin or a hydroxymethyl resin. The preparation of the hydroxymethyl resin is described by Bodansky et al., *Chem. Ind.* (London) 38, 1597–98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1–6.

Cys protected by BOC and by p-methoxybenzyl is coupled to the chloromethylated resin according to the procedure of Monahan and Gilon, *Biopolymer* 12, pp 2513–19, 1973. Following the coupling of BOC-(p-methoxybenzyl) (Cys) to the resin support, the α-amino protecting group is removed, as by using trifluoroacetic acid(TFA) in methylene chloride, TFA alone or HCl in dioxane. The deprotection is carried out at a temperature between about 0° C. and room temperature. Other standard cleaving reagents and conditions for removal of specific α-amino protecting groups may be used as described in Schroder and Lubke, "The Peptides," 1 pp 72–75 (Academic Press 1965).

After removal of the α-amino protecting group of Cys, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are: (1) carbodiimides, such as N,N'-diisopropyl carbodiimide, N-ethyl-N'-(3-dimethylaminopropyl)carbodiimide; (2) cyanamides such as N,N'-dibenzylcyanamide; (3) keteimines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) nitrogen-containing heterocyclic compounds having a hydroxy group on one ring nitrogen, such as N-hydroxyphthalimide, N-hydroxysuccinimide and 1-hydroxybenzotriazole (HOBT). Other activating reagents and their use in peptide coupling are described by Schroder and Lubke supra, in Chapter III and by Kapoor, *J. Phar. Sci.*, 59, pp 1–27 (1970).

Each protected amino acid or amino acid sequence is introduced into the solid phase reactor in about a fourfold excess, and the coupling is carried out in a medium of dimethylformamide (DMF):CH$_2$Cl$_2$ (1:1) or in DMF or CH$_2$Cl$_2$ alone. In cases where incomplete coupling occurred, the coupling procedure is repeated before removal of the α-amino protecting group prior to the coupling of the next amino acid. The success of the coupling reaction at each stage of the synthesis is monitored by the ninhydrin reaction, as described by E. Kaiser et al., *Anal. Biochem.* 34, 595 (1970).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$ and $X^8$ and the α-amino protecting group $X^1$, to obtain the peptide in its linear form. The cyclic form of the peptide is obtained by oxidizing using a ferricyanide solution or the like in accordance with known procedures, or preferably as described Rivier et al., *Biopolymers*, Vol. 17 (1978), 1927–38.

As an alternative route, the intermediate peptide may be separated from the resin support by alcoholysis after which the recovered C-terminal methyl ester is converted to the acid by hydrolysis. Any side chain protecting groups may then be cleaved as previously described or by other known procedures, such as catalytic reduction (e.g. Pd on $BaSO_4$) using conditions which will keep the Trp moiety intact. When using hydrogen fluoride for cleaving, anisole and methylethyl sulfide are included in the reaction vessel for scavenging.

The following Example sets forth the preferred method for synthesizing somatostatin-28 by the solid-phase technique, and it will be of course be appreciated that the synthesis of a correspondingly shorter peptide is effected in the same manner by merely eliminating one, two or the last three amino acids to be added to the chain.

EXAMPLE I

The synthesis of somatosatin-28 having the formula:

H—Ser—Ala—Asn—Ser—Asn—Pro—Ala—Met—Ala—Pro—Arg—Glu—Arg—Lys—Ala—

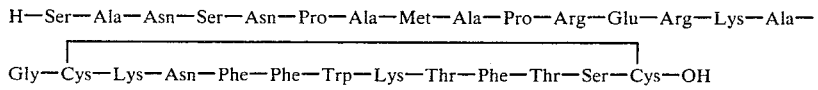

Gly—Cys—Lys—Asn—Phe—Phe—Trp—Lys—Thr—Phe—Thr—Ser—Cys—OH is conducted in a stepwise manner on a chloromethylated resin, such as that available from Lab Systems, Inc., containing 0.9 Meq Cl. Coupling of BOC-(p-methoxybenzyl) Cys to the resin is performed by the procedure set forth by Monahan et al. in *Biopolymers*, Volume 12 (1973) pp. 2513–2519, and it results in the substitution of about 0.40 mmol. Cys per gram of resin. All solvents that are used are carefully degassed, preferably by sparging with an inert gas, preferably helium, to insure the absence of oxygen that might undesirably oxidize the sulfur of the Met residue.

After deprotection and neutralization, the peptide chain is built step-by-step on the resin. Deprotection, neutralization and addition of each amino acid is performed in general accordance with the procedure set forth in detail in the aforementioned Guillemin et al. patent. Briefly, one mmol. of BOC-protected amino acid in methylene chloride is used per gram of resin, plus one equivalent of 2 molar DCCI in methylene chloride, for two hours. When Trp or Arg is being coupled, a mixture of 10% DMF and methylene chloride is used. Bzl is used as the hydroxyl side-chain protecting group for Ser and Thr. P-nitrophenyl ester (ONp) is used to activate the carboxyl end of Asn, and BOC-Asn-(ONp) is coupled overnight using one equivalent of HOBt in a 50% mixture of DMF and methylene chloride. 2-chlorobenzyloxycarbonyl (2 Cl-z) is used as the protecting group for the Lys side chain. Tosyl is used to protect the guanidino group of Arg, and the glutamic carboxyl group is protected as the Bzl ester. At the end of the synthesis, the following composition is obtained $X^1$-Ser($X^2$)-Ala-Asn-Ser($X^2$)-Asn-Pro-Ala-Met-Ala-Pro-Arg($X^3$)-Glu($X^4$)-Arg($X^3$)-Lys($X^5$)-Ala-Gly-Cys($X^6$)-Lys($X^5$)-Asn-Phe-Phe-Trp-Lys($X^5$)-Thr($X^7$)-Phe-Thr($X^7$)-Ser($X^2$)-Cys($X^6$)-$X^8$

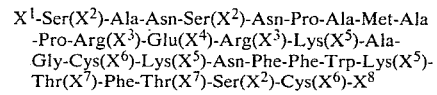

wherein $X^1$ is BOC, $X^2$ is OBzl, $X^3$ is tosyl, $X^4$ is benzyl ester, $X^5$ is 2 Cl-Z, $X^6$ is p-methoxybenzyl, $X^7$ is OBzl and $X^8$ is —O—$CH_2$-benzene-polystyrene resin support.

In order to cleave and deprotect the resulting protected peptide-resin, it is treated with 1.5 ml. anisole, 0.25 ml. methylethylsulfide and 10 ml. hydrogen fluoride (HF) per gram of peptide-resin, at −20° C. for one-half hour and at 0° C. for one-half hour. After elimination of the HF under high vacuum, the resin-peptide is washed alternately with dry diethyl ether and chloroform and then extracted with de-gassed 2 N aqueous acetic acid. Lyophilization of the acetic acid extract provides a white fluffy material.

The cleaved and deprotected peptide is then dissolved in 1% acetic acid and added dropwise to a potassium ferricyanide solution to form the disulfide bond between the Cys residues, as described by Rivier et al. in *Biopolymers*, Volume 17 (1978) pp. 1927–1938. After cyclization, the peptide is chromatographed on both anion- and cation-exchange resins using the methods described in the Rivier et al. article and then lyophilized.

The peptide is then purified by CM-32 carboxymethyl cellulose (Whatman) cation-exchange chromatography (1.8×18 cm., $V_{bed}$=50 ml.) using a concave gradient generated by dropping 1 L. of 0.5 M $NH_4OAc$, pH 6.5 into a mixing flask containing 400 ml. 0.01 M. $NH_4OAc$, pH 4.5. Final purification is carried out using partition chromatography on Sephadex G-50 fine support (Pharmacia) with a n-BuOH:pyridine:0.1% HOAc (5:3:11) solvent system. The chromatographic fractions are carefully monitored by TLC, and only the fractions showing substantial purity were pooled.

The somatostatin-28 peptide which was synthesized and purified in the foregoing manner had a specific optical rotation of $[\alpha]_D^{23°} = -81.7° \pm 0.5$ (c=1 in 1% acetic acid) and had a purity of greater than 97%. To check whether the precise sequence was achieved, the somatostatin-28 was subjected to 28 degradative cycles in a Beckman 890C sequencer using a Beckman 0.1 M Quadrol program (No. 121078). The results from the sequencer showed that the precise 28-residue peptide structure had been obtained.

The shorter 25-residue somatostatin was synthesized and purified using the same method as set forth above, and it exhibited a specific optical rotation of $[\alpha]_D^{23°} = -76.3° \pm 0.5$ (c=1 in 1% acetic acid).

EXAMPLE II

To determine the effectiveness of the peptides to inhibit the release of growth hormone, in vitro assays are carried out using both somatostatin-28 and somatostatin-25 in side-by-side comparison with equimolar concentrations of somotostatin having a known effectiveness to inhibit the release of growth hormone by pituitary cells. Cultures are used which include cells of rat pituitary glands removed some four to five days previously. Both cultures of a defined standard medium and cultures which are considered optimal for the secretion of growth hormone, as a result of having additions of either 2% or 10% of serum from a foetal calf, are used for the comparative testing between either somatostatin and somatostatin-28 or between somatostatin and somatostatin-25.

The statistical analysis of the results is carried out generally in accordance with the EXBIOL program reported in the article by Sakiz, *Excerpta Medica,* Int. Cong. Ser. No. 83 (1964), pp. 225–229. The results of this comparative testing shows that, in equimolar ratios, synthetic, substantially pure somatostatin-28 is between 3 and 14 times more effective than somatostatin and synthetic, substantially pure somatostatin-25 is between 4 and 13 times more effective than somatostatin, depending upon the particular experimental conditions of dosage and cell cultures, in inhibition of the basal in vitro secretion of growth hormone. Additional in vivo experiments show that somatostatin-28 and somatostatin-24 are also much more active than somatostatin to inhibit the secretion of growth hormone stimulated by the administration of morphine to rats.

Somatostatin-28 and somatostatin-25 are considered to inhibit basal and stimulated insulin and glucagon secretion in mammals, including humans and dogs.

These peptides also are believed to have a direct effect upon the pancreatic cells to inhibit insulin and glucagon release. Accordingly, the administration to mammals of an effective amount of either somatostatin-28 or somatostatin-25 (or a non-toxic, pharmaceutically acceptable addition salt thereof) can be used to inhibit the release of insulin and glucagon in mammals and may be employed in the treatment of diabetes in the same general manner as somatostatin is presently being administered. Likewise, administration of these peptides to mammals in effective amounts can inhibit the release of growth hormone and can be used for this purpose, under the guidance of a physician, and for the treatment of acromegaly in accordance with clinical procedures heretofore developed using somatostatin and analogs thereof.

Synthetic Somatostatin-28 and Somatostatin-25 or the nontoxic addition salts thereof, combined with a pharmaceutically acceptable carrier to form a pharmaceutical composition, may be administered to mammals, including humans, either intravenously, subcutaneously, intramuscularly or orally. The administration may be employed by a physician to inhibit the release of growth hormone where the host being treated requires therapeutic treatment for excess secretion of somatotropin, which is associated with conditions such as juvenile diabetes and acromegaly. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as addition salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 2 to about 200 micrograms of the peptide per kilogram of the body weight of the host. Overall, treatment of subjects with these peptides is generally carried out in the same manner as the treatment using somatostatin itself.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications in the 14-member somatostatin chain, which appears at the carboxyl terminal of the peptide, can be made in accordance with the well-known developments to date that have created more potent analogs of the tetradecapeptide somatostatin and such peptides are considered as being within the scope of the invention. For instance, D-Trp can be substituted for Trp, e.g. [D-Trp$^{22}$]-SS-28, to produce an increase in potency as in the case of the tetradecapeptide. [D-Trp$^{22}$]-SS-28 exhibits very substantial increases in potency with respect to the inhibition of growth hormone secretion.

Various features of the invention are emphasized in the claims which follow.

What is claimed is:

1. A pharmaceutical composition comprising synthetic somatostatin-28, synthetic somatostatin-25 or the nontoxic addition salts thereof, and a pharmaceutically acceptable liquid or solid carrier therefor.

2. A method of inhibiting the release of growth hormone in a mammal, which comprises administering to said mammal an effective amount for inhibiting growth hormone release of a material selected from the class consisting of somatostatin-28, somatostatin-25 and the nontoxic acid addition salts thereof.

3. A method in accordance with claim 2 wherein said administering is carried out either orally, intravenously, subcutaneously or intramuscularly.

4.

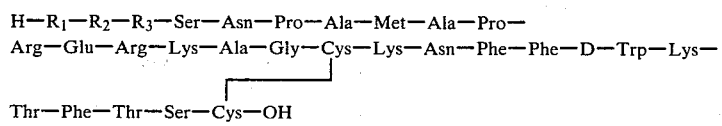

wherein $R_1$ is Ser or des $R_1$; $R_2$ is Ala or des $R_2$; and $R_3$ is Asn or des $R_3$; having a purity of at least about 95%, or the linear version thereof where the disulfide bridge is replaced by hydrogen.

5. A pharmaceutical composition comprising [D-Trp$^{22}$]-somatostatin-28 or a nontoxic addition salt thereof and a pharmaceutically acceptable liquid or solid carrier therefor.

6.

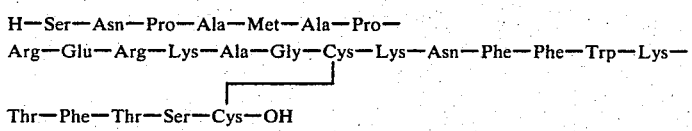

having a purity of at least about 95%, or the linear version thereof where the disulfide bridge is replaced by hydrogen.

* * * * *